US00PP10515P

United States Patent [19]

Lemon

[11] Patent Number: Plant 10,515

[45] Date of Patent: Jul. 21, 1998

[54] VARIETY OF GERANIUM PLANT NAMED 'SWEET DREAMS'

[75] Inventor: David Lemon, Lompoc, Calif.

[73] Assignee: John Bodger & Sons Company, So. El Monte, Calif.

[21] Appl. No.: 724,701

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 8,089 1/1993 Craig ..... Plt./87.12

*Primary Examiner*—Howard J. Locker

*Attorney, Agent, or Firm*—Fulwider Patton Lee & Utecht, LLP

[57] ABSTRACT

The cultivar is characterized by the distinctive light salmon color of the bloom over medium green zoned foliage. Its quick rooting time and continuous flowering provides for superb cuttings and for quick recovery of the bloom following wet weather conditions. The cultivar exhibits improved outdoor performance over the current variety Pink Camelia, and an abundant amount of cuttings may be obtained from a single plant.

2 Drawing Sheets

BACKGROUND OF THE NEW PLANT

The present invention comprises a new and distinct cultivar of *Pelargonium×hortorum* known by the varietal name Sweet Dreams (Oglevee No. 3084, Bodger No. 2GM 247-3). The new variety was discovered in a selective breeding program by David Lemon at Bodger Seeds, Ltd., Lompoc, Calif. The new variety is a selection from the crossing of Jubilee (U.S. Plant Pat. No. 8,089) which is characterized by a watermelon colored flower and medium green zoned foliage, with Bodger No. 1 GM 89-1 (unpatented) which is a salmon seedling, as distinguished from the claimed cultivar which has vari-colored salmon pink flowers and medium green zoned foliage.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWINGS

The accompanying drawings illustrate the new cultivar, the colors depicted being as nearly true as possible with color illustrations of this type.

Sheet 1 represents a side view of the new cultivar.

Sheet 2 is a view of the plant from above.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 1, 1996 and flowering on approximately Mar. 14, 1996 under full light and greenhouse, and colorings were taken indoors under 200–220 foot candles of fluorescent cool white light using the R.H.S. Colour Chart of The Royal Horticultural Society of London.

The Plant

Classification:

*Botanical.*—*Pelargonium×hortorum.*

*Commercial.*—Zonal Florist's Geranium Sweet Dreams (Florist's geraniums are a high quality plant which also grows well outdoors).

Form: Cascading mound; uniform.

*Height.*—16.0–18.0 cm above media surface.

*Growth.*—Free basal branching.

*Strength.*—No artificial support needed.

Foliage: Stalked leaf attachment, zone present.

Leaves:

*Size.*—8.0–9.5 cm.

*Shape.*—Reniform; cordate base.

*Margin.*—Crenate.

*Texture.*—Pubescent; slightly reflective.

*Color.*—Top: Green group 141B. Bottom: Green group 138B. Zone: Green group 137A.

*Ribs and veins.*—Palmate venation: Color: Yellow-green group 146D.

Petioles:

*Length.*—5.0–7.5 cm.

*Color.*—Yellow-green group 146B.

Stem:

*Color.*—Yellow-green group 146C.

*Internodes.*—3.0 cm–5.0 cm.

The Bud (Umbel)

Shape: Upright, hemispherical cluster.

Size: 2.5–4.5 cm across.

Inflorescence

Blooming habit: Semi-double; continuous, free and early flowering.

Borne: Umbel; florets on pedicel, pedicel on peduncle; 4.5–8.0 cm above foliage.

Closed florets:
*Bud size.*—1.2–1.6 cm in length; 0.8–1.0 cm in width.
Size:
*Fully open bloom.*—10–12 cm.
Open florets:
*Form.*—Slightly cupped; 12–15 florets per inflorescence open at one time, with 34 total including buds.
*Color.*—Top: Young bloom: Red group 49D; Base: Red group 38A. Bottom: Red group 49C. Old Bloom: Red group 55D. Base: Red group 49A. Bottom: Red group 55D.
*Petals.*—9–10.
*Size.*—2–2.5 cm.
*Texture and appearance.*—Smooth, satiny; appearance from a distance is a light salmon bloom above medium green zoned foliage.
Petaloids:
*Quantity.*—3–4.
*Shape.*—Twisted; irregular.
*Color.*—Upper: Tip: 49D red group. Base: 38A red group. Bottom: 49C red group. Lower: Red group 49D.
Pedicel:
*Length.*—3.0–4.0 cm.
*Color.*—At top: Red group 46A; Base: Yellow-green group 144B.
Peduncle:
*Length.*—16.5–18.0 cm .
*Color.*—Yellow-green group 146C.
Persistence:
*Disease resistance.*—Not known.
*Lasting quality.*—Unknown.

Reproductive Organs

Stamens:
*Anthers.*—Length: 1 mm.
*Filaments.*—Length: 5–6 mm. Color: White.
*Pollen.*—Brownish purple.
Pistils:
*Number.*—1.
*Length.*—8.0–9.0 mm.
*Stigma.*—Color: Purple; 5–6 parted.
*Style.*—Length: 2 mm.
Ovaries: Color: Green superior, pubescent. Length: 4–5 mm.
Fruit: None.

General Characteristics

Sweet dreams is an improvement over the current variety Pink Camelia (unpatented) which is characterized by a light salmon-pink flower with medium green zoned foliage. Cutting production, rooting time, and outdoor performance are all improved. While the bloom color of Sweet Dreams is almost identical to Pink Camelia, the addition of a stronger zone on the medium green foliage is an added bonus.

I claim:

1. A new and distinct variety of Geranium plant, substantially as shown and described.

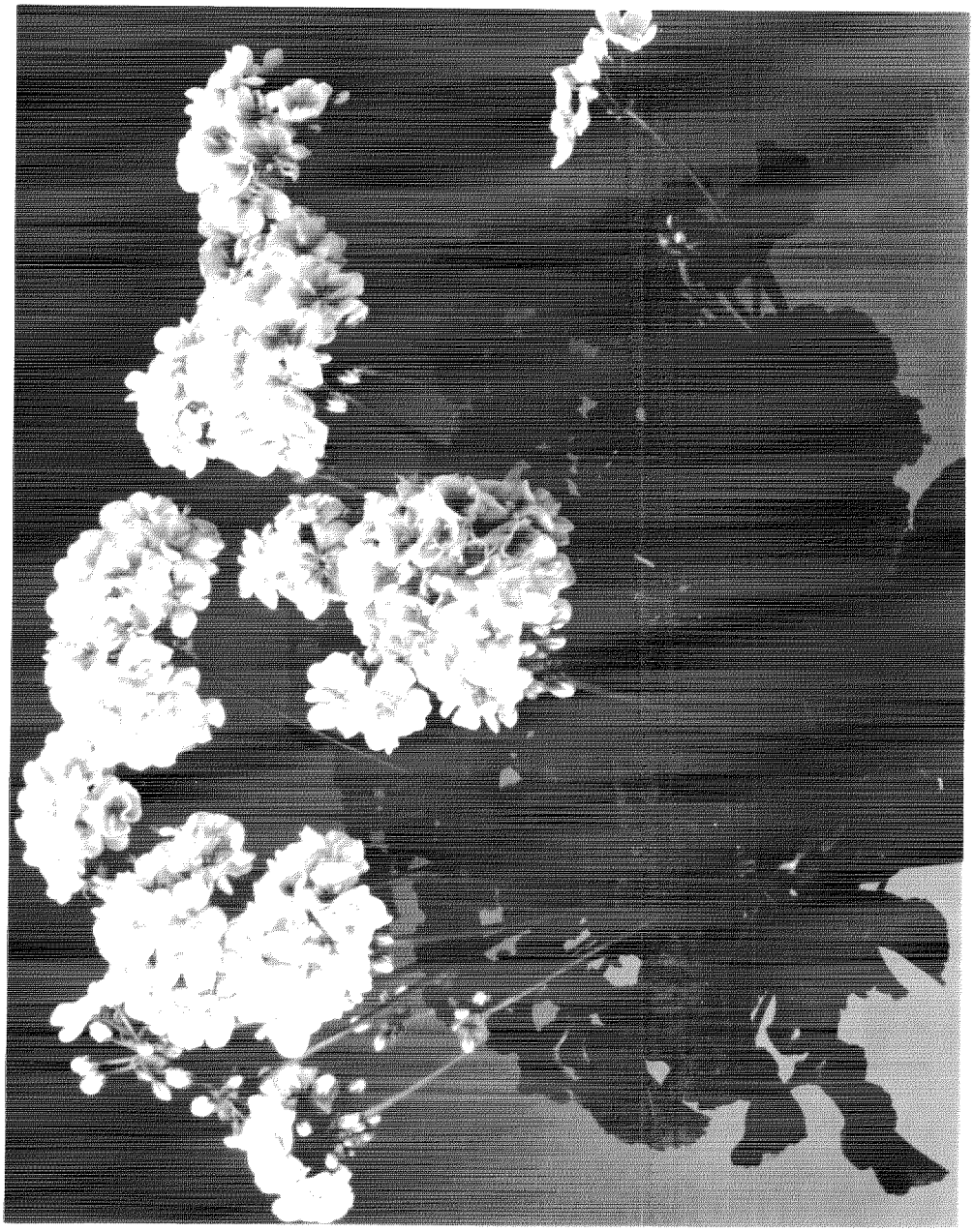

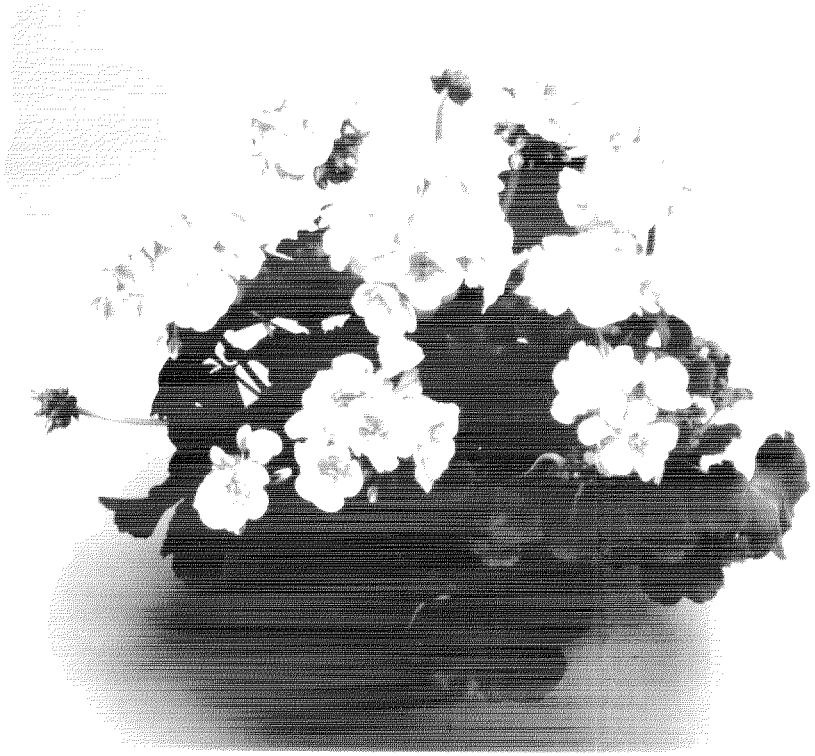

* * * * *